United States Patent [19]

Fleming

[11] Patent Number: Plant 7,445

[45] Date of Patent: Feb. 12, 1991

[54] KALANCHOE PLANT NAMED WESTERN RED

[75] Inventor: Margaret M. Fleming, Soquel, Calif.

[73] Assignee: The Plant Company, Soquel, Calif.

[21] Appl. No.: 385,163

[22] Filed: Jul. 26, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Wester Red particularly characterized by its clear red flower color that does not fade; flower diameter of 15–17 mm at maturity; flowering response, from 10 weeks in summer to 12 weeks in winter after start of short days; very floriferous with excellent display of many flowers; good keeping quality of flowers and foliage; excellent branching with or without pinching; vigorous vegetative and inflorescence growth; responsiveness to B-9 to reduce internode length and peduncle elongation; and adaptability to various pot sizes.

2 Drawing Sheets

1

The present invention relates to a new and distinctive cultivar of Kalanchoe plant, botanically known as *Kalanchoe blossfeldiana* Poelln., and referred to by the cultivar name Western Red.

Western Red, identified as 403-253, is a product of a planned breeding program which had the objective of creating new Kalanchoe cultivars for year-round commercial production having an earlier flowering response, good branching yet compact flowering, suitable for flowering in pots ranging from 10 to 15 cm, and good flower and foliage keeping quality.

Western Red was originated from a cross made by the inventor Margaret M. Fleming in a controlled breeding program in Half Moon Bay, Calif., in 1983.

The female parent of Western Red was the cultivar identified as Cinnabar, disclosed in U.S. Plant Pat. No. 5,160. The male parent was the cultivar identified as Pollux, disclosed in U.S. Plant Pat. No. 4,816.

Western Red was discovered and selected as one flowering plant within the progeny of the stated cross by Margaret M. Fleming in September of 1984 in a controlled environment in Half Moon Bay, Calif.

The first act of asexual reproduction of Western Red was accomplished when vegetative cuttings were taken from the initial selection in January of 1985 in a controlled environment in Half Moon Bay, Calif., by Margaret M. Fleming.

Horticultural examination of controlled flowerings of successive plantings has shown that the unique combination of characteristics as herein disclosed for Western Red are firmly fixed and are retained through successive generations of asexual reproduction. Western Red has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Western Red, which, in combination, distinguish this Kalanchoe as a new and distinct cultivar:

2

1. Clear red flower color that does not fade.
2. Flower diameter of up to 15–17 mm at maturity.
3. Flowering response from 10 weeks in summer to 12 weeks in winter.
4. Very floriferous with excellent display of many flowers.
5. Good keeping quality of flowers and foliage.
6. Excellent branching with or without pinching.
7. Vigorous vegetative and inflorescence growth.
8. Responsive to B-9 to reduce internode length and peduncle elongation.
9. Proper scheduling makes this new cultivar suitable for production in 10 cm to 15 cm pots.

The accompanying colored photographic drawings show typical inflorescence and leaf characteristics of Western Red, with colors being as nearly true as possible with illustrations of this type.

Sheet 1 is a color photograph showing in perspective view a plant of Western Red grown as a non-pinched flowering Kalanchoe in a 10 cm pot.

Sheet 2 is a black and white photograph showing the leaves of Western Red at three stages of development (mature, intermediate and immature).

Of the commercial cultivars known to the inventor, the most similar in comparison to Western Red is the cultivar identified as Inspiration, disclosed in U.S. Plant Pat. No. 5,899. Similar traits are flower color, plant habit and vigor, responsiveness to B-9 and adaptability to various pot sizes. In comparison to Inspiration, Western Red has a faster flowering response by one week, has a larger display of longer keeping flowers, and smaller and more durable foliage.

In comparison to the female parent Cinnabar, the flowering responses are comparable, with both varieties considered to be early. Western Red is more vigorous and branches more freely than Cinnabar, and the foliage of Western Red is smaller, more narrow, a deeper green, and more durable. The flower color of Western Red is a bright red, as opposed to the orange-red flower color of Cinnabar. The flower diameter of Western Red is somewhat smaller, but the inflorescence of Western Red is greater and more long lasting, with more buds being open at one time.

In comparison to the male parent Pollux, the foliage of Western Red is similar in form, color and size to that of Pollux, although observations to date indicate that Western Red is more resistant to Powdery Mildew. The flower size of Western Red is larger, although the respective flower colors are quite similar. Perhaps the greatest difference between Western Red and Pollux is the increased vigor and much earlier response of Western Red. To produce a finished saleable plant of Western Red from an unrooted cutting in a 15 cm. pot requires 3–5 weeks less than Pollux, a very significant commercial difference. The more vigorous Western Red attains the required linear vegetative growth 1–3 weeks sooner than Pollux, and flowering response (from start of short day treatment to flowering) is 2–3 weeks earlier for Western Red.

In the following description color references are made to The Royal Horticultural Society Color Chart. The color values were determined on plant material grown as a non-pinched pot plant in a 10 cm pot in Soquel, Calif., on Aug. 9, 1988.

Classification:

*Botanical.*—*Kalanchoe blossfeldiana* Poelln. cv. Western Red.

*Commercial.*—Flowering pot Kalanchoe.

Parentage:

*Female parent.*—Cinnabar.

*Male parent.*—Pollux.

Propagation:

(A) *Type cutting.*—Short tip cutting, with stems up to 2 cm.

(B) *Time to root.*—10 days at 21° C. in summer, 14 days at 21° in winter.

(C) *Rooting habit.*—Many very fine roots, fibrous.

Plant description:

(A) *Form.*—Vigorous, upright growth. Growing and scheduling practices can produce a small plant in a 10 cm pot up to a larger plant in a 15 cm pot.

(B) *Habit of growth.*—Rate of growth fast for this type of plant. Generally, shoots are formed at every node.

(C) *Height.*—The overall plant height of Western Red at the time of flowering ranges from 20 cm. to 30 cm. when grown in a 10 cm. pot based on the direct sticking of an unrooted cutting of two nodes and a growing tip, and with a schedule of 4–6 weeks of long day treatment (LDT) prior to the start of short day treatment (SDT), no pinch, and three to four applications of B-9 SP 3500 ppm rate.

(D) *Foliage description.*—Leaves simple, opposite, slightly lobed. 1. Size: Average full grown leaf in a 10 cm flowering pot is 115 mm long×70 mm wide. 2. Shape: Ovate to elliptic, apex obtuse to slightly pointed, base attenuate. 3. Texture: Glabrous, coriaceous, succulent. 4. Margin: Sinuate to crenate. 5. Color: Mature foliage: Upper surface 147A; Under surface 147B.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds will continue for two months or more. Individual flowers last two weeks or more after opening.

(B) *Flowering response.*—Flowering time under controlled daylength after start of short days is 10 weeks in summer to 12 weeks in winter.

(C) *Flowers borne.*—Compound dichasial cymes; peduncle length depends upon schedule, environmental conditions, B-9 applications, location upon the plant, and inherited vigor. The peduncle length range is 5 cm. to 15 cm., with the longest peduncle supporting the central inforescence. The intermediate lengths are laterals originating at lower nodes, and the shortest come from less mature nodes higher on the central axis. The peduncle diameter depends upon the same noted parameters, and ranges from 3 mm. to 7 mm. at the base, above the last pair of leaflets. Pedicel length ranges from 5 mm. to 7 mm., depending upon the same factors, including B-9 applications.

(D) *Quantity of flowers.*—Highly floriferous; although the number of flowers per plant is primarily dependent upon growing conditions, the main inflorescence and primary laterals of Western Red may each carry more than 100 flowers open at any one time. The center flower buds in any given inforescence are the first to bloom, with flowering continuing for weeks and months from buds that were not visible at first flowering.

(E) *Buds.*—The buds of Western Red are typical for Kalanchoes, growing with maturity to 12 mm. to 17 mm. in length, elliptical to oblong in shape and then developing to tubular as petals mature; buds are sheathed with four (4) green sepals.

(F) *Petals.*—1. Shape: Slightly pointed to almost round. 2. Color: Upper surface: 44A. Under surface: Closest to 38C, heavily streaked with 44A to 44B. 3. Number of petals: 4, united in corolla. 4. Flower diameter: Ranges from 15 mm. to 17 mm. when fully opened; growing conditions do not greatly influence flower diameter except that a flowering plant in declining maturity has fewer buds and open flowers, but each flower may be slightly larger than the flowers during the prime flowering period.

(G) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

Disease resistance: Resistant to Botrytis and Powdery Mildew. In addition, there have not been observed chlorosis, necrotic spots, tip die-back, stem rot, or root rot. To date, Western Red has been trouble free.

Fragrance: No perceptible fragrance of flowers or foliage.

I claim:

1. A new and distinct plant of Kalanchoe named Western Red, as described and illustrated.

* * * * *

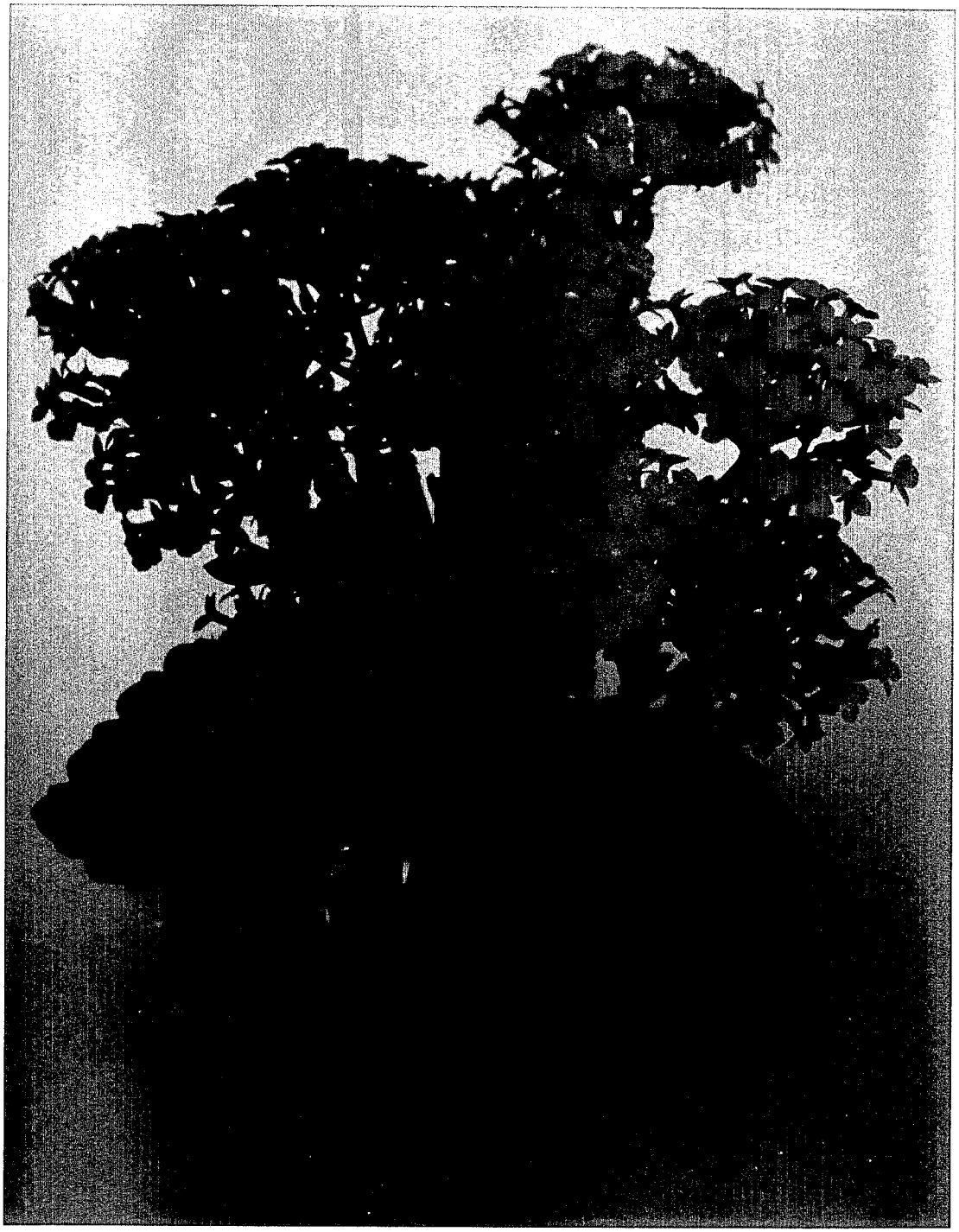

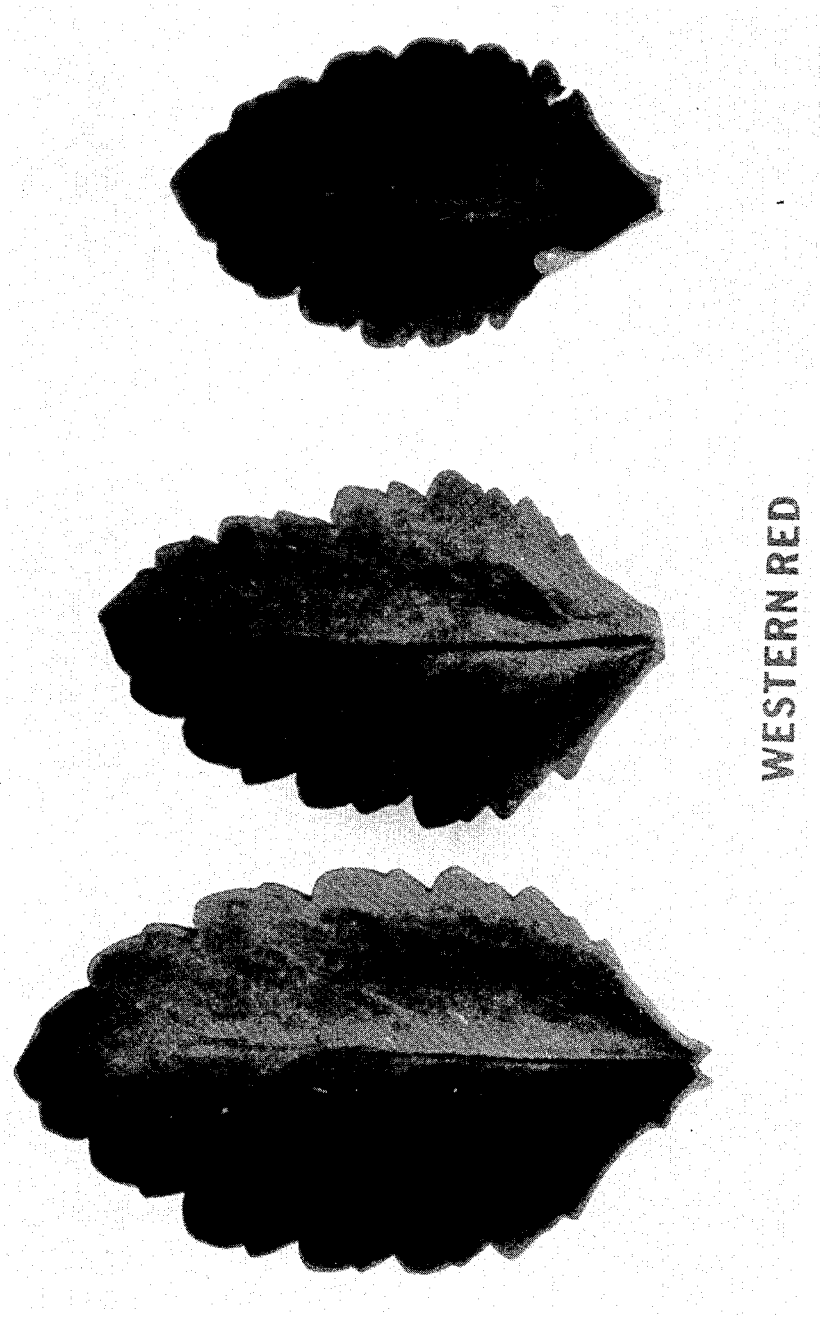
WESTERN RED